United States Patent [19]

Brassel et al.

[11] 4,338,824

[45] Jul. 13, 1982

[54] METHOD OF ADJUSTING A GIVEN PRETENSION IN THREADS ON TENSILE STRENGTH TESTING APPARATUS AND THE LIKE

[75] Inventors: Peter Brassel, Uster; Rudolf Zingg, Duebendorf, both of Switzerland

[73] Assignee: Zellweger, Ltd., Uster, Switzerland

[21] Appl. No.: 164,941

[22] Filed: Jul. 1, 1980

[30] Foreign Application Priority Data

Sep. 21, 1979 [CH] Switzerland ........................ 8546/79

[51] Int. Cl.³ .............................................. G01N 3/08
[52] U.S. Cl. .................................................... 73/828
[58] Field of Search ........................ 73/828, 830, 789

[56] References Cited

U.S. PATENT DOCUMENTS

| 464,766 | 12/1891 | Wendler | 73/830 |
|---|---|---|---|
| 2,033,623 | 3/1936 | Freeland | 73/830 |
| 2,621,512 | 12/1952 | Guimbretiere et al. | 73/830 |
| 2,875,609 | 3/1959 | Seney | 73/789 |
| 3,379,054 | 4/1968 | Folweiler | 73/828 |

Primary Examiner—Anthony V. Ciarlante
Attorney, Agent, or Firm—Craig and Antonelli

[57] ABSTRACT

A method of adjusting a given pretension in threads on tensile strength testing apparatus. A force measuring device is used as an adjusting member for the pretension, from where the tensile load increases and the elongation thereby appearing is measured. The loose thread inserted into the thread clamp is either pretensioned by means of a movable testing clamp, or the thread is stretched by a transport device until the force measuring device indicates the given pretension value.

5 Claims, 4 Drawing Figures

METHOD OF ADJUSTING A GIVEN PRETENSION IN THREADS ON TENSILE STRENGTH TESTING APPARATUS AND THE LIKE

BACKGROUND OF THE INVENTION

The invention relates to a method of adjusting a given pretension in threads on tensile strength testing apparatus and the like.

Testing methods on automatic tensile strength testing apparatus are extensively standardized, i.e., the starting conditions, under which a test is carried out, are determined by recognized instructions in order to obtain the same preconditions for all tests. In addition to the clamping length, deformation velocity, moisture and temperature of the surrounding atmosphere among other factors, the pretension which the thread should exhibit at the start of the test is also a determined value, since the stress-strain values are greatly dependent on this pretension. Also, the thread should be able to be clamped when it is stretched.

A known tensile strength testing apparatus produces, for example, a certain pretension of the inserted thread by means of a calibrated thread brake over which the thread is passed between a supply bobbin and a transport clamp of the insertion mechanism. By correspondingly adjusting the braking force of the thread brake, the thread is inserted into the testing clamps under this tension. After closing the clamps, the stretching process commences at this pretension.

Other arrangements use a yarn balance for the thread to be inserted, so that the desired pretension is imparted to the thread.

However, these known arrangements have various disadvantages. Thread brakes exert a braking force on the thread which can only be defined with difficulty, and it is difficult to achieve a change in the thread tension; circumstances permitting, auxiliary devices have to be used to determine the actual thread tension. Deflection eyelets or the like of such auxiliary devices may also falsify the measuring result. Yarn balances are also very costly and are complicated mechanisms which require a constant or periodic maintenance.

SUMMARY OF THE INVENTION

The present invention seeks to avoid these disadvantages by providing a method of adjusting a given pretension in threads on a tensile strength testing apparatus and the like, which apparatus includes a thread insertion mechanism and a pair of thread clamps, one of which is connected to a force measuring device. In accordance with the invention, the thread clamps secure the thread which is initially inserted into the thread clamps and after at least one of the thread clamps has been closed, the initial tension is measured by the force measuring device.

The method of the invention is based on the consideration that a force measuring device of the type which is used in a tensile strength measuring apparatus is a precision measuring device. This is not only to be used to determine the tensile stress, but may also be used to establish a pretension at the start of the test with the same precision. Thereby, all frictional influences which emanate from the thread guide members are also maintained at a distance from the effectively-measured thread tension.

Due to the variety of the elongations already appearing under the pretension, it is impossible to compensate these by means of a corresponding curtailment of the clamping length $E_o$.

BRIEF DESCRIPTION OF THE DRAWING

Various embodiments of the invention will now be described with reference to the accompanying drawings in which.

DETAILED DESCRIPTION OF THE PREFERRED EMBODIMENT

Figure 1:
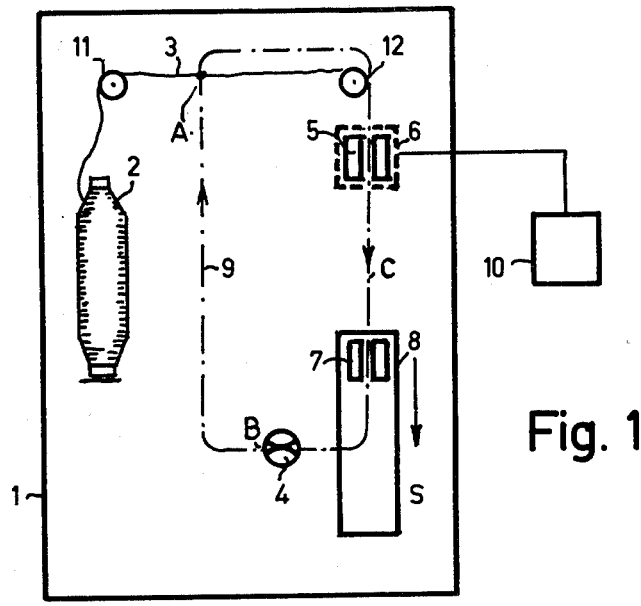
FIG. 1 schematically illustrates a tensile strength testing apparatus, including insertion means, of the type which may be used in the performance of the present invention.

In a tensile strength testing apparatus, indicated schematically by its outline 1 in FIG. 1, a thread 3 to be tested is drawn off from a bobbin 2, passed over deflection eyelets 11, 12 and inserted into the actual testing track between a measuring clamp 5 and a drawing clamp 7 by an automatic insertion apparatus, such as the one disclosed in the Roos U.S. application Ser. No. 167,027, filed July 9. 1980, and assigned to the same assignee as the present application.

The deflection eyelets 11 and 12 are used for guiding the thread, as well as tensioning it to a certain extent, which contributes to the thread being inserted into the testing stretch between clamps 5 and 7 in a tensioned condition with, for example, loop formations being avoided.

For this purpose, the apparatus includes an insertion mechanism which comprises a transport or insertion clamp 4 which travels on a suitable insertion path 9, catches a piece of thread for example at A, positions it via the deflection eyelet 12 between the measuring clamp 5 or alternatively the drawing clamp 7 and releases the thread again at B.

Since the deflection eyelets 11 and 12 only exert a slight braking effect on the thread 3, the thread is usually only inserted between the clamps 5 and 7 with a slight initial tension $V_1$ (which should be less than the selected pretension $V_2$). However, it is also possible, i.e., if the thread 3 becomes entangled when drawn off from the bobbin 2, that the initial tension $V_1$ is already greater during insertion than the prescribed pretension $V_2$. In this case, the drawing clamp 7 must first of all be drawn closer to the measuring clamp 5 until the correct pretension $V_2$ is attained, whereupon the actual tensile stress may commence.

The bobbin 2 may also be replaced by a suitable bobbin magazine from which a desired number of thread pieces may be removed from several bobbins. However, this does not have any influence on the method of the present invention.

The testing apparatus is preferably so arranged that the measuring clamp 5 is connected to a substantially-stationary dynamometer 6 while the drawing clamp 7 is movable along a path 8 and produces the elongation of the thread 3. The tensile stress values recorded by the dynamometer 6 are processed in an evaluation device 10.

A cycle of a tensile strength test runs such that after measuring clamp 5 and drawing clamp 7 are closed, the latter clamp is moved downwards whereby the tension P in the clamped piece of thread C increases from the original value of $V_1$. This behavior is shown graphically in FIG. 2. The path S of the drawing clamp 7 is shown along the abscissa 20, and the tensile force or thread tension P is shown on the ordinate 21. Reference numeral 22 indicates a given pretension $V_2$. Starting from the value $P=V_1$ for $S=0$, this thread tension P initially increases according to curve 23 at least approximately linearly with an increasing path S. Upon attaining the value $V_2$—the point of intersection with the indicated magnitude 22 of the pretension—this value is now used in the evaluation device as a threshold value so that the measurement of the tensile force acting on the dynamometer 6 is used as the initial position 0 for the further increase of the tensile force.

Figure 3:
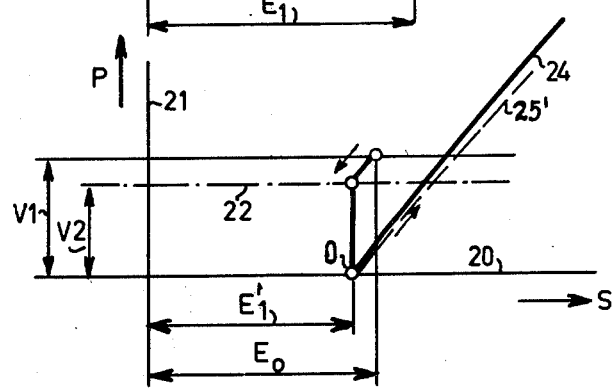

If, at the beginning of the test, the dynamometer 6 already establishes a thread tension $V_1$, which is higher than the pretension $V_2$, the drawing clamp 7 must first of all be moved towards the measuring clamp 5 until the pretension $V_2$ is attained or is not met (FIG. 3). Thereupon, the drawing clamp 7 can again be moved in the direction of increasing thread tension P and when the tensile stress has passed through the value of the pretension $V_2$, the normal tensile procedure force measurement of the thread corresponding to the stress-strain diagram 24 may take place.

In contrast to the known mechanical apparatus, this method has the following advantages: (1) the adjustment of the pretension is faster and more precise;

(2) it does not require any additional mechanical devices;

(3) the pretension values to be adjusted are reproducible at any time; and (4) any pretension value whatsoever may be selected which is within the measuring range of the force measuring device.

Figure 2:
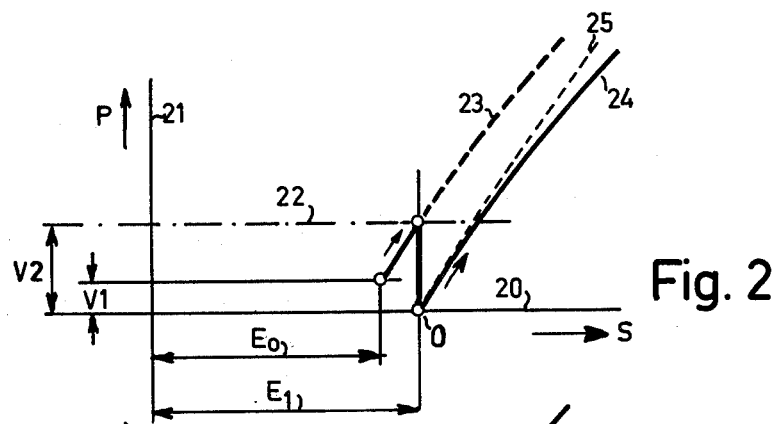
FIGS. 2 and 3 are load diagrams for a thread.

As a result of the elongation which the loose thread 3, clamped at less pretension or greater pretension than $V_2$ between the measuring clamp 5 and the drawing clamp 7, undergoes until the pretension $V_2$ is attained, the actual testing length is slightly changed. Therefore, as a basis for measuring the elongation, the clamping length $E_1$, measured upon attaining the pretension $V_2$, has to be used. This may be effected by means of a correction which takes place in the evaluation device 10. For this purpose, the measured elongations S have to be corrected with a factor which expresses the ratio of the given clamping length $E_o$ to the length $E_1$ of the pretensioned thread. In FIG. 2, a corrected stress-strain diagram of this type is indicated by reference numeral 25. In FIG. 3 reference numeral 25a characterizes the corrected stress-strain diagram for the case where the thread was inserted with too high an initial tension $V_1$ and thus had to be shortened first of all to the clamping length $E'_1$.

Figure 4:
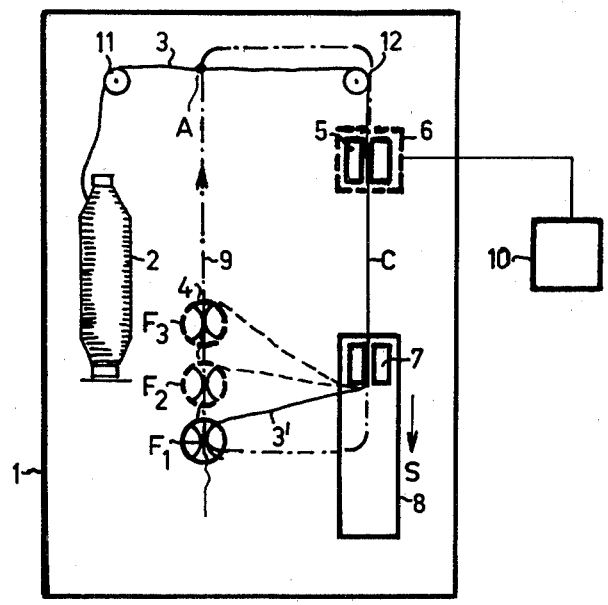
FIG. 4 schematically shows a variation of the thread insertion track.

By the method of the invention, an advantageous variation of the insertion step according to FIG. 4 may also be used. Thereby, the transport clamp 4 catches the thread 3, for example at point A, and positions it along the path 9 between the thread clamps 5 and 7. When it has arrived at $F_1$, the thread clamp 5 closes first of all. Along the section of path $F_1$ to $F_2$ of the transport clamp 4, the piece of thread 3' is relaxed since the stretched length of the thread from clamp 7 to $F_2$ is slightly shorter than that from clamp 7 to $F_1$. When the transport clamp 4 continues towards $F_3$, an additional thread length is again required but can only be obtained (since thread clamp 5 is closed) by stretching and thereby increasing the thread tension. The force measuring device 6 indicates this thread tension and generates a closing command for thread clamp 7 via the evaluation device 10 as soon as the given pretension $V_2$ is attained. Thus, the thread piece 3' is secured in the testing course C under this pretension. The rest of the testing method consists in the known increase of the thread tension by enlarging the clamp spacing, while constantly monitoring the strain appearing at the force measuring device 6.

While we have shown and described one exemplary embodiment of the present invention, it is understood that the invention is not limited thereto but is susceptible of numerous changes and modifications as are obvious to one of ordinary skill in the art, and we therefore do not wish to be limited to the details shown and described herein but intend to cover all such changes and modifications as known to those skilled in the art.

What is claimed is:

1. A method of adjusting a given pretension in threads on a tensile strength testing apparatus and the like having a thread insertion mechanism and a pair of thread clamps for securing the thread, one of which is connected to a force measuring device, comprising the steps of initially inserting the thread into the thread clamps by means of a transport clamp in the thread insertion mechanism, closing at least said one of the thread clamps, thereafter measuring the initial tension by means of the force measuring device and then applying a given pretension to the thread based on the measured initial tension by moving the thread clamps relative to each other.

2. A method according to claim 1, further including the steps of comparing the initial tension with a given pretension, moving the thread clamps relative to each other until the thread has the given pretension and then effecting the stress-strain measurement based on the established pretension.

3. A method according to claim 1, wherein said one clamp connected to the force measuring device is closed after the thread has been inserted into the thread clamps and wherein the thread piece is stretched by continued movement of the transport clamp of the thread insertion mechanism along an insertion path until the force measuring device indicates a given pretension $V_2$, whereupon the other thread clamp is closed and the transport clamp is opened.

4. A method according to claims 2 or 3, wherein the given pretension is represented as a selected threshold value, and wherein the measured value is adjusted to a starting value when the measured pretension attains said threshold value.

5. A method according to claims 1 or 2, wherein the measured value is corrected by a factor which corresponds to the ratio between the original clamping length and the thread length which appeared until the given pretension was attained.

* * * * *